United States Patent
Eglseder et al.

(10) Patent No.: US 8,210,025 B2
(45) Date of Patent: Jul. 3, 2012

(54) ARRANGEMENT AND METHOD FOR PROTECTIVE-GAS MEASUREMENT

(75) Inventors: Erich Eglseder, Kirchdorf/Krems (AT); Andreas Leonhartsberger, St. Florian/Linz (AT)

(73) Assignee: Fronius International GmbH, Petterbach (AT)

( * ) Notice: Subject to any disclaimer, the term of this patent is extended or adjusted under 35 U.S.C. 154(b) by 358 days.

(21) Appl. No.: 12/449,609

(22) PCT Filed: Feb. 8, 2008

(86) PCT No.: PCT/AT2008/000044
§ 371 (c)(1),
(2), (4) Date: Aug. 17, 2009

(87) PCT Pub. No.: WO2008/101264
PCT Pub. Date: Aug. 28, 2008

(65) Prior Publication Data
US 2010/0011837 A1    Jan. 21, 2010

(30) Foreign Application Priority Data
Feb. 22, 2007  (AT) ................................. A 279/2007

(51) Int. Cl.
*G01N 7/00* (2006.01)
(52) U.S. Cl. ....................................................... 73/23.2
(58) Field of Classification Search .................... 73/23.2
See application file for complete search history.

(56) References Cited

U.S. PATENT DOCUMENTS

| | | | |
|---|---|---|---|
| 4,733,050 A | 3/1988 | Grafius | |
| 5,329,092 A | 7/1994 | Weaver et al. | |
| 5,442,155 A | 8/1995 | Nihei et al. | |
| 6,091,048 A * | 7/2000 | Lanouette et al. | 219/130.21 |
| 6,248,975 B1 * | 6/2001 | Lanouette et al. | 219/130.21 |
| 6,524,740 B1 * | 2/2003 | Broy et al. | 429/61 |
| 6,563,085 B2 * | 5/2003 | Lanouette et al. | 219/130.5 |
| 6,723,955 B2 * | 4/2004 | Thielmann | 219/136 |

(Continued)

FOREIGN PATENT DOCUMENTS
DE        26 01 251         7/1977
(Continued)

OTHER PUBLICATIONS
International Search Report.

*Primary Examiner* — John Fitzgerald
*Assistant Examiner* — Rodney T Frank
(74) *Attorney, Agent, or Firm* — Collard & Roe, P.C.

(57) ABSTRACT

The invention relates to an arrangement and a method for measuring a protective gas (8) used in an arc-welding process by analyzing the protective gas (8) escaping from a gas nozzle (27) of a torch (10), wherein at least one sensor (31) is arranged in an external measuring device (30) for protective-gas analysis. For rapid, exact and practical determination and correspondingly effective evaluation of the protective effect of the protective gas, at least one sensor (31) is arranged in an external measuring device (30) for protective-gas analysis, which sensor (31) is positioned at a distance (38) from the torch (10) which substantially equals the distance (38) between the torch (10) and a workpiece (16) in a welding process so that the escape and effect of the protective gas (8) of an actual welding process can be simulated, and that at least one sensor (31) is connected to an evaluation unit (32) and via the latter to a welding device (1).

14 Claims, 6 Drawing Sheets

U.S. PATENT DOCUMENTS

| | | |
|---|---|---|
| 6,783,054 B1 * | 8/2004 | Pregeant et al. ............... 228/102 |
| 6,852,949 B2 * | 2/2005 | Lanouette et al. ......... 219/130.5 |
| 2004/0026392 A1 | 2/2004 | Feichtinger et al. |
| 2006/0169745 A1 | 8/2006 | Prock |

FOREIGN PATENT DOCUMENTS

| | | |
|---|---|---|
| DE | 239 744 | 10/1986 |
| DE | 251 305 | 11/1987 |
| JP | 56-056782 | 5/1981 |
| JP | 56-109187 | 8/1981 |
| JP | 61-027171 | 2/1986 |
| JP | 61-033766 | 2/1986 |
| JP | 62-234668 | 10/1987 |
| JP | 01-228675 | 9/1989 |
| JP | 09-076062 | 3/1997 |

* cited by examiner

ARRANGEMENT AND METHOD FOR PROTECTIVE-GAS MEASUREMENT

CROSS REFERENCE TO RELATED APPLICATIONS

This application is the National Stage of PCT/AT2008/000044 filed on Feb. 8, 2008, which claims priority under 35 U.S.C. §119 of Austrian Application No. A 279/2007 filed on Feb. 22, 2007. The international application under PCT article 21(2) was not published in English.

The invention relates to an arrangement for measuring a protective gas used in an arc-welding process by analyzing the protective gas escaping from a gas nozzle of a torch, wherein at least one sensor is arranged in an external measuring device for protective-gas analysis Furthermore, the invention relates to a method for measuring a protective gas used in an arc-welding process by analysing the protective gas escaping a gas nozzle of a torch.

From the prior art, several documents are known which describe protective-gas measurement.

For example, DD 251 305 A1 describes the measurement of the protective gas as regards the protective effect for the electric arc of a welding process, wherein the measurement results allow for stabilization of the welding process and quality assurance. What is disadvantageous here is that there is no precise assessment of the protective-gas properties since the protective-gas conditions are determined on basis of parameter deviations by measuring current/voltage values.

protective gas may also be measured by means of a color indicator, as described in DD 239 744 A1. Here, the color indicator changes its color as a function of the oxygen portion in the gas. What is disadvantageous here is that it takes relatively much time until the measurement result is available. Likewise, the color indicator must be changed after each measurement.

DE 26 01 251 A1 describes protective-effect measurement of an electric-arc gas atmosphere by measuring the nitrogen-oxide (NO) concentration. For analysis, the gas is sucked off a atmosphere provided about the gas nozzle by means of a suction pump. Such a suction pump as well as the corresponding components impede accessibility of the welding torch. It is likewise advantageous that such a measuring method increases gas consumption, and thus costs. Furthermore, only the NO concentration produced by the electric arc around the gas-protective area is detected, which is why the measurement is of very little informative value only. The reason therefor is that the amount of NO concentration depends on several welding parameters, e.g. electric-arc length, welding current, and the like, for which the measurement does not account.

JP 9076062 A describes a welding method in which the oxygen concentration in the vicinity of the weld is measured to avoid welding errors. The method can be used with tube welding by inserting a ring between the tubes to be welded and by inserting a sensor for oxygen-concentration measurement in the inert gas through a radial bore in the ring.

The object of the present invention is to provide for rapid, precise and practical detection and correspondingly effective evaluation of the protective effect of the protective gas. The disadvantages of the prior art shall be avoided or at least reduced.

The object of the invention is achieved in that the at least one sensor is positioned at a distance from the torch which substantially equals the distance between the torch and a workpiece in a welding process so that the escape and effect of the protective gas of an actual welding process can be simulated, and that at least one sensor is connected to an evaluation unit and via the latter to a welding device. This leads to extremely realistic measurement results for further use. It is likewise of advantage that the measuring arrangement is not subjected to the welding process, which is why the risk of impurities of and/or damage to the measurement arrangement is very low. Thanks to the connection of at least one sensor to the evaluation unit and via the latter to a welding device, the measurement results enable optimal adaptation of the gas properties to the welding processes following thereupon. The gas-supply amount can likewise be adapted to the prevailing conditions such that the precise amount of the necessary protective gas will be made available. This also allows for reduction of gas costs.

The at least one sensor is advantageously designed for measuring at least one gas property of the protective gas. This allows for conclusions as to the weld quality to be expected.

Here, at least one sensor can be formed by an oxygen sensor.

If the measuring device is combined with at least one sensor for protective-gas measurement with a cleaning unit for the wearing parts of the torch, only one station has to be activated during welding breaks, thus saving time.

It is likewise of advantage if at least one sensor is arranged in the measuring device in a position-changeable manner since this allows for different weld positions to be simulated in correspondence with the workpiece or for workpiece contours at the sensor to be reproduced (hollow weld, corner weld, vertical-down weld, overhead weld, etc.). This enables an even more precise comparison to the practical welding.

If a unit for receiving at least one sensor is provided, the measurement of the protective gas can be automated in a simpler manner, thus allowing for even more precise measurement results. This enables exterior influences in the region of the weld, e.g. air draft or component-necessitated gas-flow tolerances, to be accounted for.

In this context, the welding torch can preferably receive the receiving unit, and the protective-gas measurement occurs along the real workpiece contour.

If the receiving unit has a memory for storing the measurement results, and the memory is connected to the evaluation unit when putting the receiving unit back into the measuring device, the measurement results can be transmitted automatically to the evaluation unit.

This may also be effected by a radio module included in the receiving unit for wireless transmission of the measurement values to the evaluation unit.

According to a further feature of the invention, it is provided that the receiving unit is adapted to the distance between the welding torch and the workpiece according to a welding process.

If a preferably circular means for pressurized-air guidance is provided about at least one sensor, the sensor can be cleaned automatically by means of the pressurized air. This also allows for a simple and rapid method to be realized to measure the gas properties of the entire protective-gas atmosphere, in particular its rim region.

To this end, the means for pressurized-air guidance has a pressurized-air chamber which is provided with a connection for the pressurized air.

If the means for pressurized-air guidance has a movable ring with an outlet opening through which the pressurized air escapes the pressurized-air chamber into the direction of the at least one sensor at a defined pressure, the rim region of the protective-gas atmosphere can be measured even if the torch is fixedly mounted, e.g. on a torch slide, and is prevented from rotational movement.

By the measure of arranging at least one suction opening about at least one sensor, said suction opening being connected to a means for sucking off the protective gas, it is achieved that there will not remain any residual gases in the direct environment of the sensor which would falsify the measurement result.

If the measuring device is provided with a cover for at least one sensor, the sensor can be protected against impurities, and an influence on the measurement results by the impurities can be avoided.

Furthermore, the object of the invention is achieved by an above-mentioned method in which the torch is positioned above an external measuring device with at least one sensor for protective-gas analysis, and wherein the distance between the torch and at least one sensor is selected to be substantially the same as the distance between the torch and a workpiece in a welding process, and wherein for analysis the protective gas is caused to escape the gas nozzle as is the case in a welding process, and wherein the effect of the protective gas is measured with at least one sensor and evaluated in an evaluation unit connected to the sensor. Here, it is advantageous that the escape and effect of the protective gas of an actual welding process are simulated. This leads to extremely realistic measurement results which can be evaluated very quickly by the evaluation unit and can be made available, e.g. to the welding device, for further use.

If the effect of the protective gas is detected in the center of a protective-gas atmosphere by measuring at least one gas property of the protective gas by means of at least one sensor, the measurement is done at that point of the protective-gas atmosphere where the electric arc contacts the workpiece.

Here, the center point of a sensor can be positioned in an elongated axis of the torch and/or a welding wire extending therein for measuring the gas properties.

According to a further feature of the invention, it is provided that the effect of the protective gas is detected in the rim region of a protective-gas atmosphere by measuring at least one gas property of the protective gas by means of at least one sensor. This allows for distribution of concentration to be determined. It is likewise possible to detect partial impurities, which might be relevant or not to the respective welding process (welding direction, welding position).

To measure the gas properties, the protective-gas atmosphere can be displaced in a defined manner by means of pressurized air so that the rim region of the protective-gas atmosphere will be displaced across the at least one sensor.

In this context, the pressurized air can be caused to escape an outlet opening, and the pressure can be increased in a stepwise manner.

The escaping pressurized air can likewise be rotated about the protective-gas atmosphere so that the entire portion of the protective-gas atmosphere will be displaced gradually across the at least one sensor.

The torch can likewise be moved about a sensor in a substantially circular manner, wherein the center point of the circular movement is formed by the position of the sensor.

In this context, several circular movements about the sensor can be done with the torch with different radii.

Alternatively, or additionally, the torch can be moved about a sensor in a substantially cross-wise manner, wherein the center point of the cross-wise movement is formed by the sensor.

If a sensor is used for measuring several gas properties, measurement is necessary at one position only and can thus be done rapidly.

On the contrary, using a separate sensor for each property of the protective gas allows for more precise measurement results since the individual sensors can be adapted more precisely to the gas property to be measured.

In this context, a sensor can be formed by an oxygen sensor.

By the measure of performing a gas-property measurement after a defined number of welded welds it is achieved that the welding process is not influenced by the periodic measurements done between the welding processes.

Likewise, the measurement can be done after a cleaning of the wearing parts of the torch, thus allowing for control and/or adaptation to the gas properties to the next welding process. Likewise, quality of the protective-gas effect is assessed already before starting the next welding process.

Moreover, the measurement can be done before and after a cleaning of the welding parts of the torch, which allows for assessment of the cleaning effect. Accordingly, a second cleaning process will be optionally conducted and/or an exchange of the gas nozzle be ordered.

According to a further feature of the invention, it is provided that the currently-detected gas properties are compared to those in a memory of the evaluation unit present in the form of deposited and welding-process-adapted reference values. This enables checking of the set parameters for the protective gas at the welding device.

If a starting point of the torch, the so-called tool center point, is controlled on basis of the interrelationship between the position of the torch, of the protective-gas effect measured, and the corresponding reference values, it is always possible to obtain the precise position of the weld.

Advantageously, data are exchanged between the evaluation unit and the welding device, allowing for changes of the gas properties based on the measurement results directly after measurement, i.e. before the next welding process.

If the detected gas properties are stored in the evaluation unit after each measurement so as to allow for trend analysis, specific information can be given on when welding parts, e.g. the gas nozzle, have to be exchanged. This also allows for assessment as to until which wearing state the wearing parts can still be used effectively.

If the torch receives a receiving unit connected to at least one sensor, and the real workpiece contour is followed at a distance between the welding torch and the workpiece according to a welding process, exterior influences in the region of the weld, e.g. air draft or component-necessitated gas-flow tolerances, can be taken into account.

Advantageously, the workpiece contour is followed at a rate appropriate in a welding process. This is quite similar to the conditions during the welding process.

If the results of the protective-gas measurement are stored in a memory in the receiving unit, and if the measurement results are automatically transmitted from the memory to the evaluation unit when the receiving unit is put back into the measuring device or if the results are transmitted to the evaluation unit via a radio module arranged within the receiving unit, the measurement results of the evaluation unit are substantially immediately available.

Advantageously, conclusions are automatically drawn from the results of the evaluation unit as to the quality of the welding processes conducted and the quality of the gas properties is controlled for the welding processes following thereupon. What is advantageous here is that the measurement of the gas properties in a measuring device is of practical orientation, which ensures high-quality assessment of the gas properties as regards the weld. Thus, a precise quality assurance is possible. It is likewise of advantage that exactly these properties which are directly relevant to the weld quality are analyzed along with the evaluation of the gas properties. It is also of advantage that the state of the welding parts can be assessed on basis of the gas properties, and that the measurement of the gas properties is possible with very low protective-gas consumption. It is furthermore of advantage that no threshold values of the protective-gas composition will be exceeded.

In this context, gas properties, such as oxygen portion, nitrogen portion, carbondioxide portion, gas temperature, escape rate, degree of humidity, gas pressure, gas density, mass flow and/or volume flow or the like are measured and evaluated. This is why results can be quickly obtained and conclusions as to the weld quality can be quickly drawn.

Advantageously, impurities of the gas nozzle are concluded automatically by measuring, and evaluating, the oxygen portion of the protective gas. This allows for detection of the degree of contamination without complex optical methods. Thus, an exchange and/or cleaning of wearing parts will only be done if really necessary.

Furthermore, conclusion can be drawn automatically as to the use of a correct gas nozzle after a change of wearing parts by measuring, and evaluating, at least the gas pressure and the rate of the protective gas. This ensures a quality which is always the same.

Moreover, conclusions are drawn automatically as to the effect of a cooling circuit of the torch by measuring the temperature of the protective gas. This protects the torch against getting overheated.

If conclusions are drawn automatically as to the temperature of the hose pack and the torch by measuring the temperature of the protective gas, the torch and the hose pack can be protected against too high temperatures at the beginning of the welding process. This is also very gentle to the wearing parts.

Automatically drawing conclusions as to the pores in the weld to be welded and to the welded weld by measuring the degree of humidity of the protective gas allows for assessment of whether a pore formation has occurred or whether the pore formation lies within a tolerance limit. The pore formation is one quality characteristic for the weld.

Finally, conclusions can be drawn automatically to defect components of the protective gas by measuring the mass flow of the protective-gas components. This allows for detection of gas loss and cost saving.

The present invention will be explained in more detail by way of the enclosed schematic drawings. Therein:

Initially, it is pointed out that same parts of the exemplary embodiment are denoted by the same reference numbers.

FIG. 1 depicts a welding apparatus 1 or welding plant for various welding processes or methods such as, e.g., MIG/MAG welding or WIG/TIG welding, or electrode welding methods, double-wire/tandem welding methods, plasma or soldering methods etc.

Figure 1:
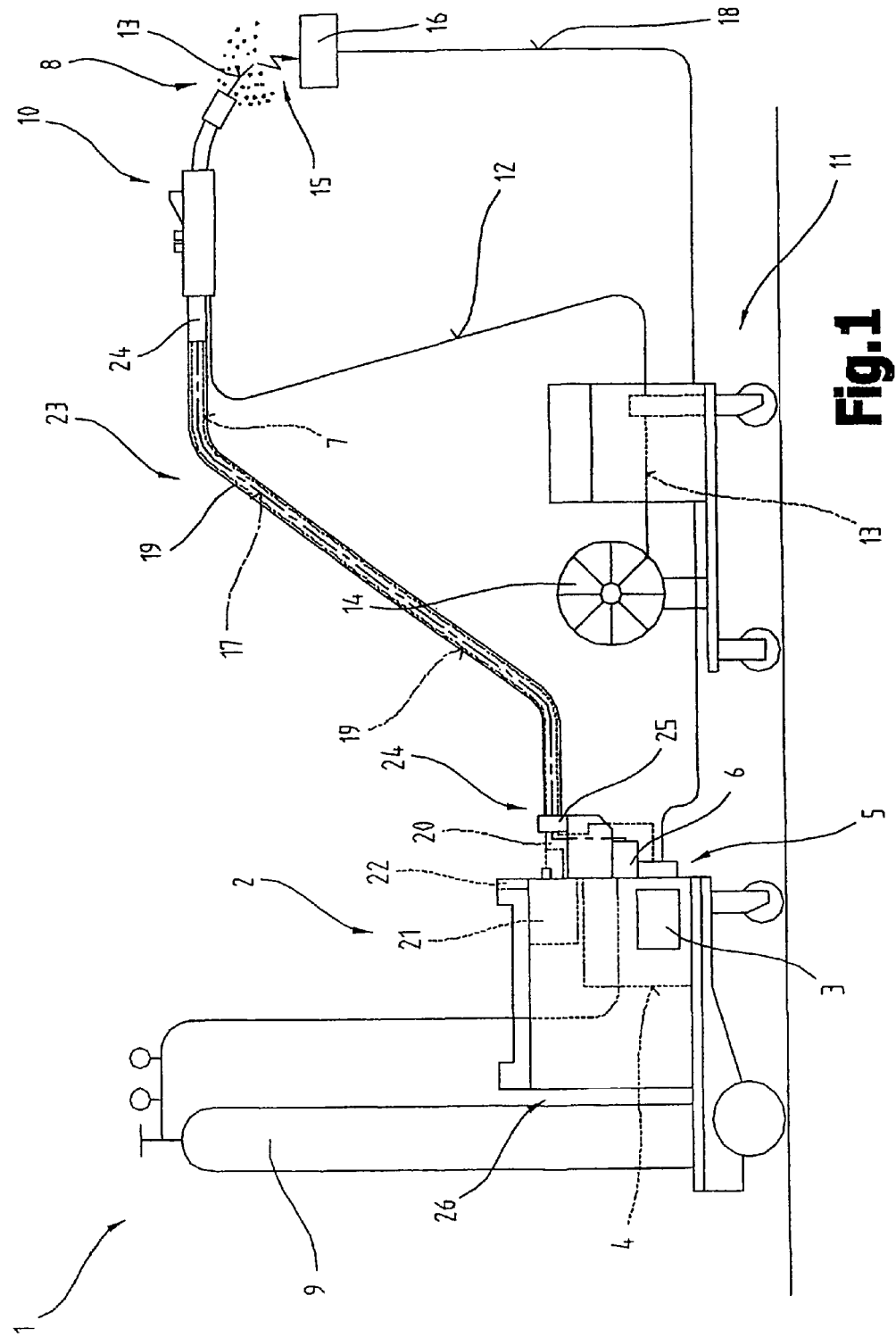
FIG. 1 shows a schematic representation of a welding apparatus or a welding device.

The welding device 1 comprises a power source 2 including a power element 3, a control device 4, and a switch member 5 associated with the power element 3 and the control device 4, respectively. The switch member 5 and the control device 4 are connected to a control valve 6 arranged in a supply line 7 for a gas 8, in particular, a protective gas such as, e.g., $CO_2$, helium or argon and the like, between a gas reservoir 9 and a welding torch 10, or torch.

Besides, a wire feeder 11 as is usually employed in MIG/MAG welding can also be activated by the control device 4, wherein additional material or welding wire 13 is fed from a feed drum 14, or wire coil, into the region of the welding torch 10 via a feed line 12. It is, of course, possible to integrate the wire feeder 11 in the welding device 1 and, in particular, its basic housing, as is known from the prior art, rather than designing the same as an accessory device, as is illustrated in FIG. 1.

It is also feasible for the wire feeder 11 to supply the welding wire 13, or additional material, outside the welding torch 10 to the process site, to which end a non-consumable electrode is preferably arranged in the welding torch 10, as is usually the case with WIG/TIG welding.

The power for building up an electric arc 15, particularly an electric arc for welding, between the non-consumable electrode (not illustrated) and a workpiece 16 is supplied from the power element 3 of the power source 2 to the welding torch 10 and, in particular, electrode via a welding line 17, wherein the workpiece 16 to be welded, which is formed of several parts, is likewise connected with the welding device 1 and, in particular, power source 2 via a further welding line 18, thus enabling a power circuit for a process to build up over the electric arc 15 or plasma jet formed.

To provide cooling of the welding torch 10, the welding torch 10 may be connected with a fluid reservoir and, in particular, water reservoir 21 by a cooling circuit 19 via an interposed flow control 20, whereby the cooling circuit 19 and, in particular, a fluid pump used for the fluid contained in the water reservoir 21, is started as the welding torch 10 is put into operation, in order to effect cooling of the welding torch 10.

The welding device 1 further comprises an input and/or output device 22, via which the most different welding parameters, operating modes or welding programs of the welding device 1 can be set and called, respectively. In doing so, the welding parameters, operating modes or welding programs set via the input and/or output device 22 are transmitted to the control device 4, which, in turn, will subsequently activate the individual components of the welding plant or welding device 1, and predefine the respectively desired control values.

In the exemplary embodiment illustrated, the welding torch 10 is, furthermore, connected with the welding device 1 or welding plant via a hose pack 23. The hose pack 23 accommodates the individual lines leading from the welding device 1 to the welding torch 10. The hose pack 23 is connected with the welding torch 10 via a coupling device 24, whereas the individual lines arranged within the hose pack 23 are connected with the individual contacts of the welding device 1 via connection sockets or plug-in connections. In order to ensure an appropriate strain relief of the hose pack 23, the hose pack 23 is connected with a housing 26 and, in particular, the basic housing of the welding device 1 via a strain relief means 25. It is, of course, possible to use the coupling device 24 also for the connection to the welding device 1.

Basically, it is to be noted that not all of the aforementioned components need be used or employed in the various welding methods or welding devices 1, such as, e.g., WIG devices or MIG/MAG devices or plasma devices. In this context it is, for instance, feasible to design the welding torch 10 as an air-cooled welding torch 10.

Furthermore, the welding torch 10 comprises a gas nozzle 27 which encloses the electrode 13, with the protective gas 8 continuously escaping said gas nozzle 27 during a welding process. This is why a protective-gas atmosphere 28 is permanently provided about the electric arc 15 so that the latter and the molten metal region of the workpiece 16 can be protected from the outer atmosphere 29. This allows for the air oxygen and/or the ambient air to be kept away from the weld during a welding process, thus protecting the liquid metal below the electric arc 15 against oxidation which would otherwise weaken the weld. The result of a protective-gas welding process thus is a weld of very high quality. To this end, the user or welder usually adjusts the escape amount of the protective gas 8 only quantitatively and based on these experiences, or the adjustment relies on the instructions made in the manual, so as to provide for a sufficiently good protective-gas atmosphere 28 for the electric arc 15. The extent to which the electric arc 15 and the molten metal region are protected from the outer atmosphere 29, changes as a function of the protective-gas escape amount, the state and the manner in which the protective gas 8 escapes and/or of the protective-gas distribution when the protective gas is escaping the gas nozzle 27. In practice, the distribution of the protective gas 8 is frequently affected by weld spatters adhering inside of the gas nozzle 27 or by dirt since this causes more ambient air to enter the protective-gas atmosphere 28, thus deteriorating weld quality. This is why measurement of the oxygen portion of the protective gas 8 is advantageous for the quality of the welding process.

According to the invention, it is now provided that the protective-gas measurement is done via at least one sensor 31 arranged in a measuring device 30. To this end, a sensor 31 can be designed such that it detects the properties of the protective gas 8, such as the oxygen portion, and forwards them to a corresponding evaluation unit 32 for evaluation.

Figure 2:
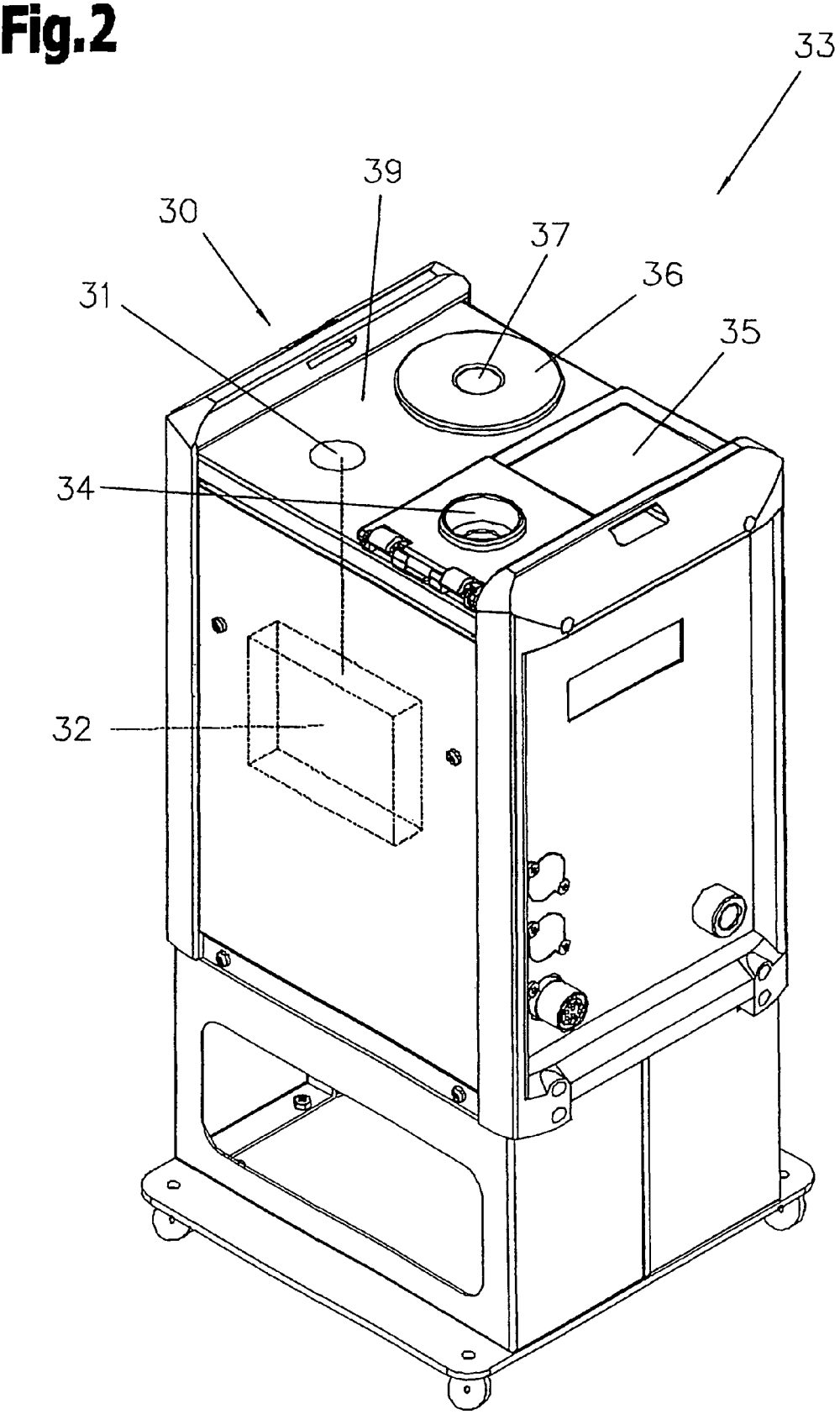
FIG. 2 shows a perspective view of a cleaning unit with the inventive measuring arrangement.

According to FIG. 2, the measuring device 30 is preferably integrated into an external cleaning unit 33 so that the at least one sensor 31 is arranged therein as well. The cleaning unit 33 may also be formed by a maintenance station or the like for the welding torch 10 or integrated in such a maintainable station. This combination allows for the welding breaks needed for so-called maintainable intervals to be shortened since only one station has to be activated, e.g. by a robot.

The cleaning unit 33 serves for cleaning the welding torch 10, wherein primarily the wearing parts of the welding torch 10, in particular the gas nozzle 27 are cleaned. The cleaning unit 33 can have a tub 35 for the cleaning liquid into which the welding torch 10 is immersed to cool down the adhering metal spatters. In addition to the liquid tub 35, a refilling container 34 can be arranged via which the tub 35 can be supplied with liquid. A coil 36 having an opening 37 is positioned behind the tub 35. After having been immersed into the tub 35, the welding torch 10 will be placed into the opening 37 of the coil 36. After supplying the coil 36 with electric current, the metal spatters will be removed from the welding torch 10 in a contactless manner. The impurities fall into a refuse bin (not illustrated) arranged below the coil 36. Since such a cleaning unit 33 is already known from the prior art, this will not be handled in more detail.

Figure 3:
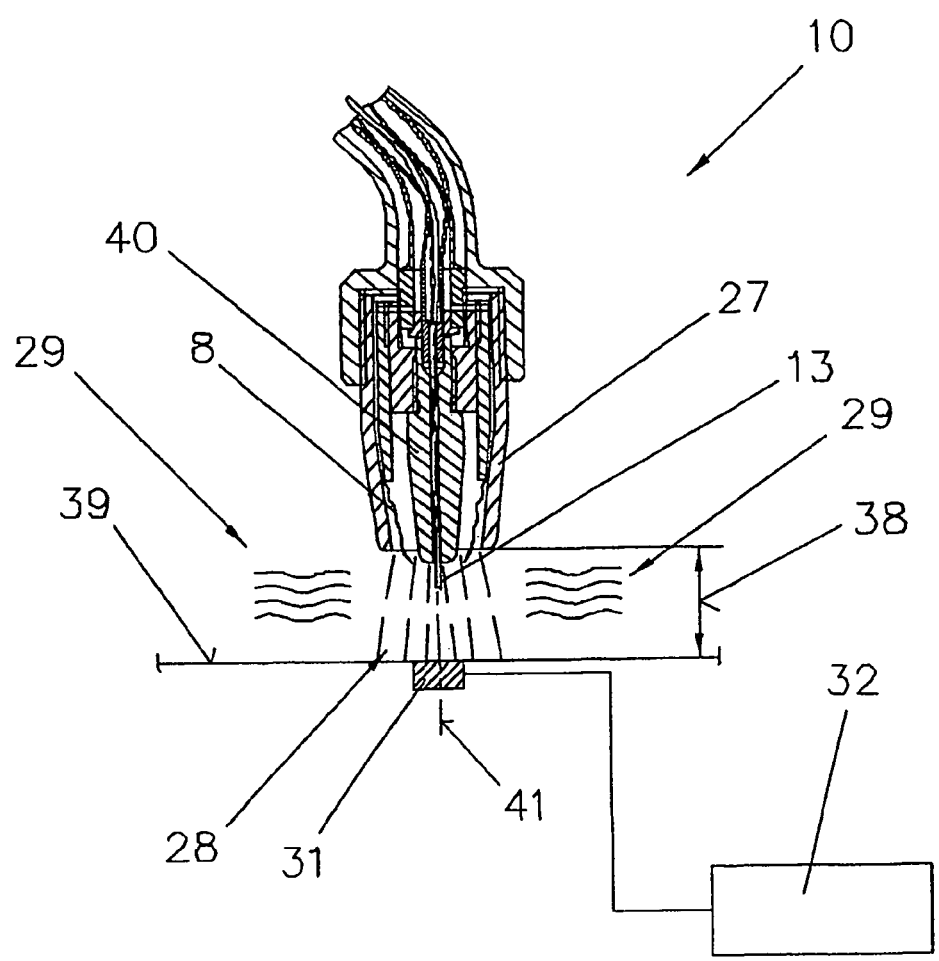
FIG. 3 shows the positioning of the welding torch for the protective-gas measurement.

According to the invention, the at least one sensor 31 for measuring the properties of the protective gas 8, such as air entrainment, temperature, flow rate, pressure, humidity or the protective-gas composition in general, is now added to the cleaning unit 33. What is advantageous here is that also the properties of the protective gas 8 can be measured in addition to the anyway cyclically conducted torch and/or nozzle cleaning. This measurement preferably allows for determination as to which weld quality is to be expected with the next welds, and as to which quality the already welded welds are. Such measurements and/or cleanings are for example done after a defined number of welds, e.g. 10 to 40, and after a defined consumption of the welding wire, e.g. 50 to 100 meters, etc. Thus, this would be a so-called offline protective-gas measurement. Yet, since the measurements and/or cleanings are done within a process cycle, one may indeed talk about a so-called online protective-gas measurement. The time additionally needed for measurement is between 2 to 10 seconds, mainly depending on the number of protective-gas properties to be measured per measurement process. To achieve that the measurement substantially corresponds to the conditions prevailing during a welding process, the welding torch 10 is arranged substantially above the sensor 31 such that there will be a distance 38 between the sensor 31 and the welding torch 10 which corresponds to the distance between the workpiece 16 and the welding torch 10, as illustrated in FIG. 3. To this end, the welding torch 10 is positioned substantially perpendicularly to the sensor 31, wherein the welding wire 13 is arranged exactly over the center point of the sensor 31. This ensures that the sensor will measure the properties of the protective gas 8 exactly where the electric arc 15 contacts the workpiece 16 during a welding process. This is achieved in that the surface 39 of the measuring device 30 forms one plane with the sensor 31. Furthermore, exactly that amount of gas is caused to escape the gas nozzle 27 for measurement that has been used for the welds welded at last and/or will be used for the next welds. This allows for exact checking whether the used torch 10 and/or the gas nozzle 27 has (have) provided for the required protective effect of the protective gas 8 for the electric arc 15 and/or whether this will be the case in the next welds. To this end, the sensor 31 will of course be appropriately calibrated.

A measurement of the oxygen portion in the protective-gas atmosphere 28 is done preferably prior to a cleaning of the welding torch so that the rather time-consuming cleaning will be conducted if need be only. To this end, a commercially available oxygen sensor can be used, e.g., for measuring the air entrainment and/or air portion in the protective gas 8. If the evaluation unit 32 detects a too high oxygen portion on basis of the measurement results and that the protective effect necessary is thus not provided, a cleaning of the gas nozzle 27 will be preferably done, as described above. This cleaning is necessary since turbulences are created in the escaping gas flow in the gas nozzle 27 because of adhering welding spatters, allowing for air oxygen to enter the protective-gas atmosphere 28. Accordingly, the welding spatters adhering inside of the gas nozzle 27 and/or the spatter ring on the end of the gas nozzle 27 will be detached during cleaning so that they will no longer produce any turbulences in the escaping gas 8. This means that no more air oxygen will enter the protective atmosphere 28, which is why the protective effect for the electric arc 15, and consequently the weld quality, will again meet the requirements. After cleaning, for example, one more measurement of the oxygen portion may be done so as to enable assessment of the cleaning result. In case of a satisfying result, the next welding processes can be done without any reservations. Yet, in case of a cleaning result not meeting the requirements, one more cleaning may be done with subsequent control measurement. This alternation between cleaning and subsequent control measurement may be done, e.g. for a defined number of times. Yet, if this alternation does not yield a satisfying result, the gas nozzle 27 must be exchanged manually. In case of automated welding systems, the cause therefor may also be a displaced tool center point, as will be described in more detail in the following. Thus, measuring the oxygen portion in the protective-gas atmosphere 28 allows for conclusions as to the degree of contamination of the gas nozzle 27.

Besides the oxygen portion, the sensor 31 can also measure the temperature, the escape rate, a degree of humidity, a pressure, a density, a mass flow and/or volume flow, the mass portion of a component, etc., of the gas 8. In general, the protective-gas measurement allows for conclusions to be drawn as to the weld quality, and for prediction of the weld quality. This quality depends on several factors, e.g. cooling of the torch 10 or supply for the protective gas 8. The influence of these individual factors on the quality of the weld can be controlled by measuring the individual protective-gas properties.

Measurement of the protective-gas temperature allows for conclusions to be drawn as to the cooling effect of the torch 10. In case of too high a measured protective-gas temperature, the necessary cooling effect is not provided which is why no further welding processes can or should be done. Thanks to this control there is also a checking of the functions of all components (pumps, lines, etc.) of the cooling circuit. Preferably, the welder is informed about a defect or the defect is appropriately displayed at the input and/or output device 22 so that the defect in the cooling circuit can be corrected, wherein further measurements may optionally be necessary for spotting the defect.

The measured degree of humidity in the protective gas 8 likewise allows for conclusions to be drawn as to the number, or frequency, of the pores in the weld. To this end, corresponding reference values are preferably deposited in the evaluation unit 32 or in the control device 4 of the welding device so as to enable assessment of whether the measured degree of humidity meets the requirements and is admissible.

The measurement of the escape rate and/or rate distribution allow(s) for conclusions to be drawn as to the state of the distribution bores which distribute the protective gas 8 when it enters the gas nozzle 27. The cause for a change in the escape rate is often welding spatters or other impurities adhering inside of the gas nozzle 27 which affect the protective effect for the electric arc 15.

The measurement of the individual protective-gas properties likewise allows for checking whether a gas nozzle 27 at the torch 10 is appropriate for the specific use or whether the used gas nozzle 27 is damaged or has been damaged during welding processes, e.g. by collision. Detection thereof preferably occurs based on the measurements of at least the gas pressure and the rate, which are directly indicative for the escape behavior of the protective gas 8 from the gas nozzle 27. This is of particular importance for the different weld positions since the geometry of the gas nozzle 27, e.g. diameter and length, determines the protective effect necessary for the electric arc 15.

The measurement of the protective gas properties likewise allows in a simple manner for measurement of the composition of the protective gas 8. Thus, it can be checked whether also the necessary composition of the protective gas 8 has been used or is used for the welded welds and/or the next welds. Accordingly, it is likewise possible to measure the protective effect of relevant gases, e.g. carbondioxide, nitrogen, argon, helium, etc.

The protective-gas atmosphere 28 also fulfils the function of protecting the direct environment of the electric arc 15 against ambient air so as to prevent the melting bath from oxidizing. For this reason, the distribution of the protective gas 8, i.e. the escape behavior, is also of importance when the gas escapes the gas nozzle 27.

In the above, it has been described how the gas properties are measured at the contact site of the electric arc 15 at the workpiece 16. There are the following possibilities for measuring, e.g., also the oxygen portion in the outer region and/or rim region of the protective atmosphere 28:

For example, several sensors 31 may be arranged such that all of the protective atmosphere 28 can be measured at once. Yet, certain movements about the one sensor 31 are done by the torch 10 mounted to a robot. This may be, e.g., a vertical and a horizontal movement which overlap at the sensor 31 or circular movements and/or movement along a curve about a sensor 31. Here, e.g. the sensor 31 forms the center point of the circle, wherein the radius will be enlarged after each complete circular movement about the sensor 31 until the gas properties are detected in the entire protective atmosphere 28.

Figure 4:
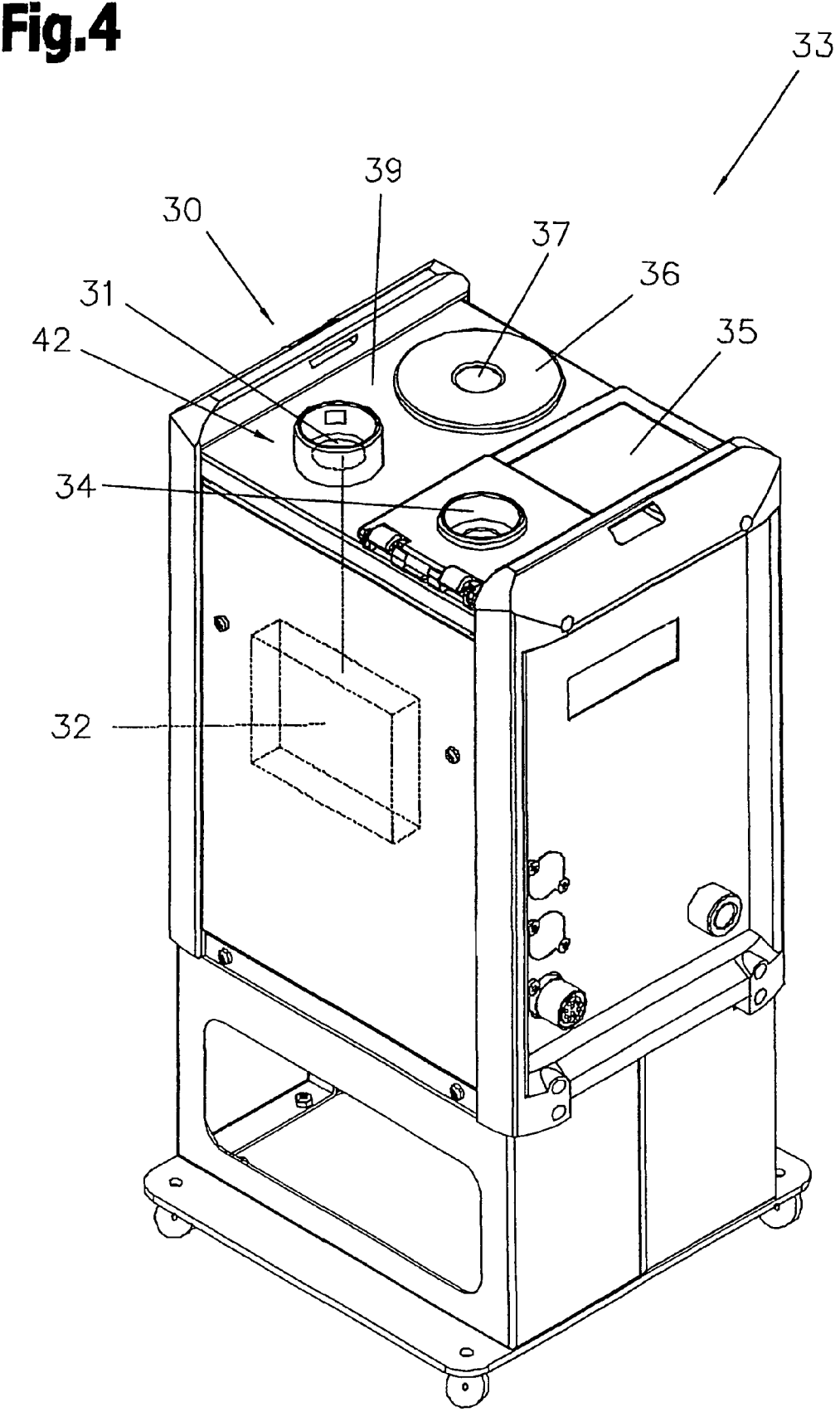
FIG. 4 shows a perspective view of a cleaning unit with the inventive measuring arrangement and pressurized-air guidance.
Figure 5:
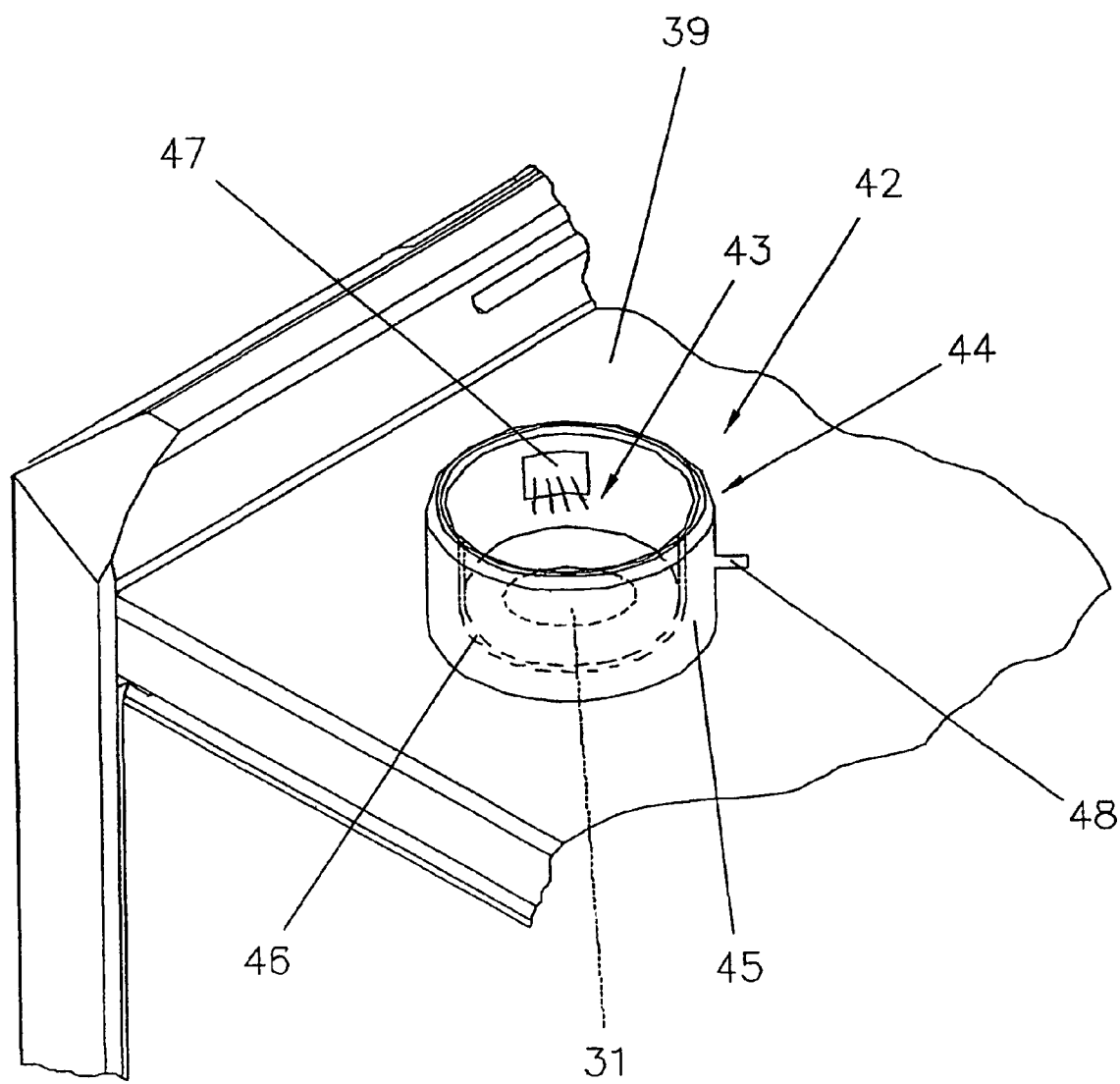
FIG. 5 shows the pressurized-air guidance in a detailed view.
Figure 6:
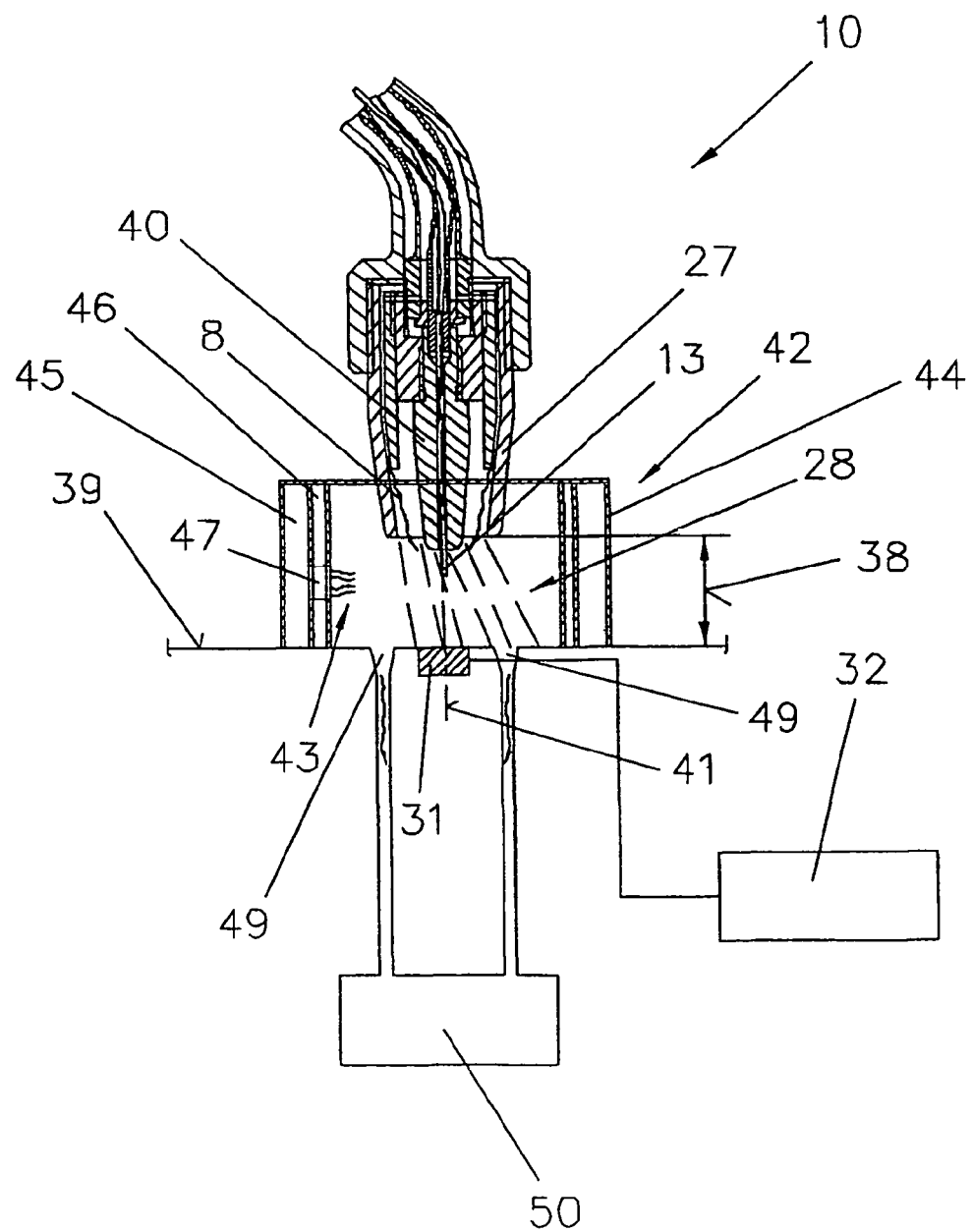
FIG. 6 shows the positioning of the welding torch for the protective-gas measurement in the pressurized-air guidance.

A further possibility of measuring the rim region of the protective-gas atmosphere 28 results from the use of a pressureized-air guidance 42, as illustrated in FIGS. 4 to 6. This guidance has the effect that substantially the protective-gas atmosphere 28 is specifically displaced by a pressurized air 43 so as to allow for the sensor 31 fixedly arranged within the measuring device 30 to measure the effect of the rim region of the protective atmosphere 28. Thus, the torch 10 and/or the gas nozzle 27, which cannot do any circular movements, e.g. so-called torch slides, can measure preferably the rim region of the protective-gas atmosphere 28. To this end, the pressurized-air guidance 42 is formed by a circular housing 44, a pressurized-air chamber 45 and a movable ring 46 with an outlet opening 47. Pressurized air 43 is supplied into the pressurized-air chamber 45 via an appropriate connection 48, with the pressurized-air chamber 45 being defined on the outside by the housing 44 and on the inside by the ring 46 so as to provide for a defined pressure. Then, the pressurized air 43 flows through the outlet opening 47 at the defined pressure so that the protective-gas atmosphere 28 will be correspondingly displaced. Preferably, escape of the pressureized air 43 is controlled by a valve integrated in the outlet opening 47. For example, to allow for an oxygen-distribution profile in the protective-gas atmosphere 28 to be established, the ring 46 is rotatably mounted. This is why the outlet opening 47 rotates about the protective-gas atmosphere 28 such that the oxygen portion in each region of the protective-gas atmosphere 28 can be detected by the fixedly mounted sensor 31. Here, it is necessary for the pressure in the pressurized-air chamber 45 to be increased in a stepwise manner so that the rim region of the protective-gas atmosphere 28 will be displaced gradually across the sensor 31. The rotation of the ring 46 is preferably effected via a motor (not illustrated). Thus, the rotational speed of the ring 46 and/or the outlet opening 47 can be adapted precisely to the escape pressure of the pressurized air 43, wherein the escape pressure in turn depends on the escape rate of the gas 8. These interrelationships are preferably deposited in the evaluation unit 32 according to the type of the welding torch 10 and/or the gas nozzle 27.

With such measures it is achieved that the gas properties can be measured on the entire surface which is created when the protective atmosphere 28 contacts the workpiece 16 and thus forms the protective area for the melting bath of the weld. For example, this also allows for detection of impurities which are only partially present in the gas nozzle 27. This is why such impurities are only detectable by including a profile, e.g. of the oxygen distribution. In case of a mean-value measurement of the oxygen concentration in the protective atmosphere 28, it would very likely not be possible to detect partial impurities.

It goes without saying that all measurement results are stored in the evaluation unit 32 or the control device 4 so that the values, distributions and profiles of the protective-gas atmosphere 28 and their properties will be available for later comparisons. Reference values may likewise be deposited for all protective-gas properties so as to allow for direct measurement checking. Storing these data also allows for a so-called trend analysis. This means observation of changes in the protective atmosphere 28 with increased duration of use of the gas nozzle 27. Based on these results, e.g., the cleaning cycle of the torch 10 and/or the gas nozzle 27 can be optimized by the effect of the protective atmosphere 28. That is to say, the number of welds which can be welded with a cleaned gas nozzle 27 increases from about 10 to 15, e.g.

Likewise, the measurement results are also directly taken into account for the settings of the welding parameters, e.g. by comparing the composition of the protective gas 8 with the composition set at the welding device 1. This also allows for the gas-flow rate, the escape rate, etc., to be adapted and/or corrected to the set values. This is of particular advantage if new wearing parts, e.g. gas nozzle 27, contact tube 40, etc., are used. Thus, defects in the protective atmosphere 28 and defects which can be concluded from the measurements can be detected in advance and remedied so that the weld quality will not get worse.

To be able to measure this variety of protective-gas properties, several sensors 31 are substantially used in practice. That is to say, the respective gas property is measured by substantially one sensor 31 each in a row. For example, this is effected by the sensor 31 being automatically exchanged after measurement of a protective-gas property. To this end, for example, 5 sensors 31 are fixed to a wheel (not illustrated) which does a rotating movement to move the respective sensor 31 such that said sensor 31 will be positioned at the contact site of the electric arc 15.

A further possibility of detecting several measurement values at once is to arrange the necessary sensors 31 in a cavity below the surface 39 of the measuring device 30. This cavity is preferably arranged instead of the sensor 31 shown in FIG. 3, wherein the cavity has one or also several openings oriented in the direction of the contact site of the electric arc 15. Through these openings, the contacting gas 8 reaches the individual sensors 31 which will then measure the individual protective-gas properties.

It goes without saying that measurement of the individual protective-gas properties (oxygen portion, temperature, degree of humidity, pressure, etc.) may alternatively also be done by one single sensor 31 which is capable of detecting all protective-gas properties at once.

To obtain precise measurement results for the weld positions to be simulated, the measuring device 30 may include, e.g., movable parts. These may then by moved in a preferably automated manner such that the weld position to be simulated, e.g. fillet weld, will be established. It goes without saying that the sensor 31 will also be moved in correspondence therewith such that the sensor 31 will be exactly in the elongated axis 41 of the electrode 13 and/or welding wire 13. This is also the case with the above-described measurements. However, since there are only slight deviations in the measurement results if the welding torch 10 is positioned to be substantially perpendicular to the surface 39, this method is the better one for practice. This is also due to the fact that this method can be implemented with substantially less effort, and thus fewer costs.

To obtain even more precise measurement results and/or to obtain measurement results adapted to the ambient conditions of the workpiece 16 to be welded, the measuring device 30 can additionally include a receiving unit (not illustrated) for the sensor 31. That is to say, the welding torch 10 is designed to receive, and fix, the receiving unit in a preferably automated manner, with the sensor 31 being subsequently received, and fixed, by the receiving unit. To this end, the sensor 31 is of course provided in an appropriate retention means so as to be received by the receiving unit.

This method has the particular advantage that the receiving unit can be adapted to the distance between the welding torch 10 and the workpiece 16 in a manner corresponding to the respective welding process, e.g. by positioning several receiving units of different length in the measuring device 30. It goes without saying that the length of the receiving unit can likewise be varied by appropriate selection of the fixing position at the torch 10.

After having fixed the sensor 31 to the welding torch 10 for measuring the gas properties, the weld to be welded can be followed appropriately along this contour. Here, protective gas 8 is appropriately caused to escape so as to be able to measure the necessary properties, as described above. The measurement results obtained here are very informative since the measurement conditions are realistic and since additional factors, e.g. air draft or component-necessitated gas-flow tolerances, are taken into account for quality assessment. It goes without saying that these factors can also be simulated at the measuring device 30, wherein such a simulation of the realistic measurement conditions would mean a high effort.

Depending on the design of the receiving unit, the measurement results can either be temporarily stored in the same or directly transmitted to the evaluation unit 32 via a radio module. In the case of temporarily stored measurement results, a memory is correspondingly integrated in the receiving unit. After having followed the workpiece contour(s), the sensor 31 and the receiving unit are again placed at the cleaning unit 33. To be now able to read the measurement results from the memory, a connection with the evaluation unit 32 is established, e.g. when positioning the evaluation unit. Here, the connection for transmitting the measurement results from all methods known in the prior art may be established.

Since the inventive measuring device 30 is placed externally, e.g. in the cleaning unit 33, it is of advantage to provide for appropriate provisions against impurities, in particular of the sensor 31. Preferably, a cover is provided which covers the sensor 31 automatically after a measurement so as to protect it against dust, welding spatters, etc. For example, the cover is a glass pane which covers the sensor 31 by a rotational movement and uncovers it for measurement. According to the inventive embodiment including the pressurized-air guidance 42, the sensor 31 can be covered, e.g. by a lid on the housing 44.

Since the sensor 31 is used only periodically for measurements, the breaks can be utilized for cleaning the sensor 31. Preferably, this cleaning is done with closed cover and by means of the pressurized air 43, thus blowing possible dirt residues which the escaping gas 8 detached during measurement out of the gas nozzle 27. Since pressurized air 43 is anyway caused to escape during measurement in the rim region of the protective-gas atmosphere 28, the sensor 31 is here also automatically cleaned during measurement.

Here, the dirt is removed preferably through a suction opening 49 provided about the sensor 31, this being preferably assisted by a suction 50, as illustrated in FIG. 6. Furthermore, the suction 50 can also be preferably used for sucking off the protective gas 8 accumulated in the measurement region about the sensor 31. This is why there will be no falsification of the next measurements.

The suction 50 can likewise be activated during a measurement so as to prevent the escaping protective gas 8 from displacing the outer atmosphere 29. For example, this would lead to no air oxygen but substantially the protective gas 8 itself being sucked into the protective-gas atmosphere 28 in case of turbulences, thus falsifying the measurement result.

According to the invention, the protective-gas properties, e.g. the oxygen portion, are substantially measured by the torch 10 positioned perpendicularly to the surface 39 and thus also to the sensor 31, wherein the distance 38 of the torch 10 to the sensor 31 is selected according to a welding process. Preferably, the invention is used with automated welding plants, i.e. a robot positions the welding torch 10 via the sensor 31. The robot does this via the tool center point (TCP) known from the prior art which serves as the starting point for the robot movements. This is why it is of importance for the TCP to be always correct. Yet, from practice it is known that the TCP may be shifted by possible collisions of the torch 10 with the workpiece 16 or the like or by heat impact. Thus, it is advantageous to check the TCP periodically, e.g. According to the invention, this feature is effected by measurement of a protective-gas property. To this end, a reference value is deposited in the evaluation unit 32 which is compared to the currently measured value. In case of a certain difference outside of a certain tolerance range, the TCP has been shifted and must be corrected and/or the control device 4 or the robot control must take this difference into account. Preferably, this is done after a cleaning of the torch 10 and/or the gas nozzle 27 so as to ensure that the deviation of the measurement has not been caused by impurities.

For example, the evaluation unit 32 can also be formed by the control 4 of the welding device 1 or can be part of a superior control of the welding plant (welding device, robot, wire feed, etc.). The evaluation unit 32 and the sensor 31 can furthermore form a unit.

It is likewise conceivable that the measuring device 30 does the protective-gas measurement also in a component of the welding plant, e.g. the wire feeder or the hose pack. Here, one purely talks about an online protective-gas measurement, with the results having less practical orientation, as if the measurement is inventively done at the same distance as in case of one welding process.

The invention claimed is:

1. An arrangement for measuring a protective gas used in an arc-welding process by analyzing the protective gas escaping from a gas nozzle of a torch, the measuring arrangement comprising:
    an external cleaning unit;
    a measuring device integrated into the external cleaning unit; and
    at least one sensor is arranged in the measuring device for protective-gas analysis, wherein the at least one sensor is positioned at a distance from the torch which substantially equals the distance between the torch and a workpiece in an actual welding process so that the escape and effect of the protective gas of an actual welding process can be simulated, and wherein the at least one sensor is for measuring at least one gas property of the protective gas and comprises an oxygen sensor connected to an evaluation unit and via the latter to a welding device so as to assess a state of a plurality of wearing parts of the torch and automatically detect a degree of contamination of the gas nozzle by measuring and evaluating an oxygen portion of the protective gas.

2. The measuring arrangement according to claim 1, wherein the at least one sensor is arranged in the measuring device in a position-changeable manner.

3. The measuring arrangement according to claim 1, wherein a circular means for guiding pressurized air is arranged about the at least one sensor.

4. The measuring arrangement according to claim 1, wherein at least one suction opening is arranged about at the least one sensor, which suction opening is connected to a means for sucking off the protective gas.

5. A method of measuring a protective gas used in an arc-welding process by analyzing the protective gas escaping from a gas nozzle of a torch, wherein the torch is positioned above an external measuring device with at least one sensor for protective-gas analysis, wherein the distance between the torch and the at least one sensor is selected to be substantially the same as the distance between the torch and a workpiece in an actual welding process, and wherein for analysis of the protective gas, protective gas is caused to escape the gas nozzle as is the case in a welding process, and wherein at least one gas property of the protective gas is measured with at least one sensor and evaluated in an evaluation unit connected to the sensor so that the escape and effect of the protective gas in case of an actual welding process will be simulated, wherein the oxygen portion of the protective gas is measured, and evaluated, as the gas property of the protective gas, and wherein conclusions are automatically drawn as to the impurities of the wearing parts of the torch.

6. The measuring method according to claim 5, wherein the effect of the protective gas is detected in the center of a protective-gas atmosphere, wherein the center point of a sensor is positioned to be in an elongated axis of the torch and/or a welding wire extending therein for measuring the gas properties.

7. The measuring method according to claim 5, wherein the effect of the protective gas is detected in the rim region of a protective-gas atmosphere by measuring at least one gas property of the protective gas by means of at least one sensor.

8. The measuring method according to claim 7, wherein the torch is moved about a sensor in a substantially circular manner, wherein the center point of the circular movement is formed by the position of the sensor.

9. The measuring method according to claim 5, wherein a sensor is used for measuring several gas properties.

10. The measuring method according to claim 5, wherein a separate sensor is used for each property of the protective gas.

11. The measuring method according to claim 5, wherein the currently-detected gas properties are compared to those in a memory of the evaluation unit present in the form of deposited and welding-process-adapted reference values.

12. The measuring method according to claim 11, wherein a starting point of the torch, the so-called tool center point (TCP), is controlled on basis of the interrelationship between the position of the torch, the protective-gas effect measured, and the corresponding reference values.

13. The measuring method according to claim 5, wherein the use of a correct gas nozzle can be concluded automatically after a change of wearing parts by measuring, and evaluating, at least the gas pressure and the rate of the protective gas.

14. The measuring method according to claim 5, wherein conclusions are drawn automatically as to the pores in the weld to be welded and to the welded weld by measuring the degree of humidity of the protective gas.

* * * * *

UNITED STATES PATENT AND TRADEMARK OFFICE
CERTIFICATE OF CORRECTION

PATENT NO.       : 8,210,025 B2
APPLICATION NO.  : 12/449609
DATED            : July 3, 2012
INVENTOR(S)      : Eglseder et al.

Page 1 of 1

It is certified that error appears in the above-identified patent and that said Letters Patent is hereby corrected as shown below:

Title Page, item [73], Assignee: please change "Petterbach (AT)" to correctly read:

--Pettenbach (AT)--.

Signed and Sealed this
Eleventh Day of September, 2012

David J. Kappos
*Director of the United States Patent and Trademark Office*